(12) United States Patent  
Prokop (10) Patent No.: US 6,589,563 B2
(45) Date of Patent: *Jul. 8, 2003

(54) DRUG DELIVERY SYSTEM EXHIBITING PERMEABILITY CONTROL

(75) Inventor: Ales Prokop, Nashville, TN (US)

(73) Assignee: Nanodelivery, Inc., Brentwood, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/256,508

(22) Filed: Sep. 27, 2002

(65) Prior Publication Data

US 2003/0035838 A1 Feb. 20, 2003

Related U.S. Application Data

(62) Division of application No. 09/752,056, filed on Dec. 29, 2000, now Pat. No. 6,482,439.
(60) Provisional application No. 60/173,503, filed on Dec. 29, 1999.

(51) Int. Cl.[7] ............................. A61K 9/16; A61K 9/14
(52) U.S. Cl. ..................... 424/490; 424/489; 424/493; 424/494; 424/496; 424/497
(58) Field of Search ................................ 424/400, 489, 424/490, 493, 494, 496, 497, 78.08, 178.1, 179.1; 428/402, 402.24; 427/212

(56) References Cited

U.S. PATENT DOCUMENTS

| 5,130,126 A | 7/1992 | Koyama et al. |
| 5,462,866 A | 10/1995 | Wang |
| 5,744,153 A | 4/1998 | Yewey et al. |

FOREIGN PATENT DOCUMENTS

| WO | WO 99/18934 | 4/1999 |
| WO | 99/18934 | * 4/1999 |
| WO | WO 99/59548 | 11/1999 |
| WO | WO 00/64954 | 11/2000 |

* cited by examiner

*Primary Examiner*—Michael G. Hartley
*Assistant Examiner*—Sharmila S. Gollamudi
(74) *Attorney, Agent, or Firm*—Alston & Bird LLP (57) ABSTRACT

Microparticles and nanoparticles prepared from oppositely charged polymers are provided in which a drug is incorporated into the core and is conjugated to one polymer by a Schiff-base crosslink. The particles are suitable for use in injectable formulations in which the rate of release of the drug through the particle shell is slowed as compared to noncrosslinked drugs. Enzymatically degradable polymers can be incorporated in otherwise hydrolytically stable particles to provide drug release at particular sites within the body where the enzyme of interest is present.

11 Claims, 3 Drawing Sheets

DRUG DELIVERY SYSTEM EXHIBITING PERMEABILITY CONTROL

CROSS-REFERENCE TO RELATED APPLICATIONS

This application is a division application of U.S. patent application Ser. No. 09/752,056, filed Dec. 29, 2000 now U.S. Pat. No. 6,482,439 and is related to commonly owened provisional Application Ser. No. 60/173,503, filed Dec. 29, 1999, and claims the benefit of its earlier filing date under 35 U.S.C. 119(e).

FIELD OF THE INVENTION

This invention relates to nanoparticulate, microparticulate, and polymeric film drug delivery systems.

BACKGROUND OF THE INVENTION

A number of polymeric formulations and polymeric structures have been proposed for a variety of drug delivery vehicles. Both synthetic polymers, which are made by man, and biopolymers, including proteins and polysaccharides, have been proposed for use as carriers for various drugs, including growth factors, genes, and other products of biotechnology. The polymeric vehicle is generally much larger than the drug to be delivered. Some of these polymeric drug delivery vehicles can be broadly categorized as nanoparticles, microparticles, and films. Nanoparticles typically are less than about one micron in diameter and generally range from about 1 to 1,000 nanometers (nm)(1 $\mu$m=1,000 nm). Normally, nanoparticles range from about 100 to 300 nm. Microparticles typically have a diameter of above about 1 micron, generally from about 1 to 2,000 $\mu$m (2 mm), normally ranging from about 100 to 500 $\mu$m. Drug delivery vehicles are also based on polymeric films, which are sometimes used as coatings. These polymeric films are generally from about 0.5 to 5 mm in thickness.

A number of different techniques have been proposed for preparing drug delivery vehicles. The drug can be encapsulated in a polymeric matrix formulation for subsequent sustained release for controlled drug delivery. Some of these techniques are limited by the use of organic solvents that may leave a residue of undesirable organic solvent in the final product. Toxic degradation products have also been found in techniques using synthetic polymers in aqueous solvents.

Drug delivery vehicles in the form of microparticles and nanoparticles are usually formed either by polymer precipitation upon addition of a non-solvent or by gelling the polymer upon addition of a small inorganic ion (salt) and a complexing polymer of an opposite charge. Several of these binary polymeric encapsulation systems, which result from two different polymers, have been described. Given sufficient time, the interior core of the polymer can be completely gelled. The inner core material is usually a polyanionic, or negatively charged, polymer and the particle membrane, or shell, is made from a combination of a polycationic polymer, which is a positively charged polymer, and a polyanionic polymer. The core polymer is usually atomized, or nebulized, into small droplets and collected in a receiving bath of an oppositely charged polymer. However, these systems tend to be characterized by a lack of flexibility in adjusting the physical properties of the particle membrane, which limits the success of these systems.

Multicomponent polymeric microparticles for encapsulation of living cells have been proposed to permit independent modification of mechanical strength and permeability. However, the relatively large size of many of these particles are drawbacks to their use as injectable drug delivery formulations.

Polymeric hydrogels have been proposed for encapsulation of living cells in the production of bioartificial organs. The hydrogel isolates the encapsulated cells from the immune system. For example, immune cells and IgG antibodies can be precluded from entering a cell or tissue implant that is encapsulated by a hydrogel polymeric barrier so that an immunogenic reaction to encapsulated foreign tissue is precluded. However, these hydrogels have a relatively high porosity that is normally suitable only for isolating larger particles. For example, a membrane used to isolate animal pancreatic islet cells can be adjusted to preclude passage of substances of molecular weight from about 70,000 to 150,000 daltons or larger. Thus, although considerable improvements have been achieved in tightening the pore size of hydrogels, generally speaking, the available pore size of hydrogels is typically unsuitable for delivering small drug molecules having a molecular weight of several hundred Daltons in a slow fashion over several days or weeks.

Several methods have been described to further slow down drug release from various polymer formulations. Gel beads can be prepared from complexes of a drug and an oppositely charged water-soluble polymer in a polyelectrolyte. The drug is released by dissociation of the drug-bead complex as the drug is exchanged with counterions present in the surrounding fluid. The release rate is constant, which means the surface area of the drug carrier is constant. Fast release rates for nanoparticles having a high ratio of surface area to volume are unacceptable for most therapeutic use.

Enzymatic release within the organism has also been proposed for delivery from macrodevices, including from drug-chitosan crosslinked beads or gel formulations. These soluble complexes can typically be applied intravenously.

Nevertheless, problems, drawbacks, and limitations persist in developing effective drug delivery systems for some medical applications, including developing injectable formulations of small drugs having site specific application.

SUMMARY OF THE INVENTION

The invention described below provides new combinations of multicomponent water-soluble polymers that enable the permeability and release rate of polymeric drug delivery vehicles to be better controlled and to control the release rate of therapeutically relevant drugs. The invention includes methods of making polymeric particles for drug delivery and for other applications in which the drug is covalently conjugated, through a persistent chemical bond or through a dissociable Schiff-base bond, with at least one polymer in a multipolymeric microcapsule, microparticle, nanoparticle, or film to slow its release rate.

For example, the invention includes polymeric complexes in which a gelling polymer and a polymer for permeability control, normally charged polymers of opposite charge, are used to slow the diffusion rate of cationically charged drugs from conjugates of these small molecule drugs with polymers. In a specific embodiment, a dissociable Schiff-base covalent conjugate is formed between dextran polyaldehyde and a small drug, which can include various proteins, growth factors, antigens, or genes in addition to synthetic or naturally occurring chemicals. Physiological reaction conditions are selected that include a dissociable Schiff-base complex that provides a slow drug release, typically from a charged multipolymeric nanoparticle or microparticle.

In another embodiment, a maleic acid anhydride-PEG polymer is used to form a Schiff-base complex with a small molecule drug. The drug-polymer conjugate is then formulated into a suitable nanoparticulate vehicle for release.

In the formation of the persistent covalent bond, a water-insoluble drug is conjugated to a water-soluble polymer to solubilize the drug. The conjugate of drug and polymer is then incorporated into a drug carrier of the invention, including nanoparticles and microparticles. The entire conjugate of drug and soluble polymer is released from the particles by diffusion or by enzymatic degradation of the delivery vehicle.

The method of the invention includes the steps for preparing the drug and polymer conjugates in multipolymeric nanoparticles, microparticles, and films. In one embodiment of the method, the method includes the steps of: providing a stream of uniformly-sized drops of a charged polymer solution in which the particle size of the drops is submicron or at most only a few microns, collecting these droplets in a stirred reactor provided with a polymeric solution of opposite charge, and reacting the droplets and the solution to form the particles. When the drops of polymer are polyanionic and the receiving polymer solution is cationic, then the particles have a polyanionic core and a shell or corona of a polyanionic/polycationic complex. The periphery of the particle has an excess positive charge. Conversely, drops of a stream of cationic solution can be collected in a polyanionic solution. These particles have polycationic core and shell of a polycationic/polyanionic complex with an excess of negative charge on the particle periphery.

In an alternative embodiment of the method, the charged polymer solutions are mixed together in the ratio of 1/1 to 1/4 and gently stirred for 5 to 10 minutes. Spontaneous formation of particles is observed for many combinations of polymer. In a further aspect of the invention, there is included a method of adjusting the rate of release of a drug or drug-polymer conjugate in situ by incorporating an enzymatically degradable polymer into an otherwise nonbiodegradable formulation. For example, chondroitin sulfate, hyaluronic acid, chitosan or a protein may be incorporated into the formulation to allow for enzymatic degradation of the particle by hyaluronidase, lysozyme, or protease(s), respectively, in bodily sites. Such formulations are of advantage in ocular, intravenous, wound-healing and cancer treatments since ocular fluids and serum contain the enzyme lysozyme and wounds and cancer areas generally contain proteases.

Water insoluble drugs can be made water soluble by application of the invention. The drug and polymer complexes prepared with water soluble polymers typically retain water solubility.

DETAILED DESCRIPTION OF THE INVENTION

"Drug" means any chemical substance used in the treatment, cure, prevention, or diagnosis of disease or otherwise to enhance the physical or mental well being of a human or other animal, regardless of molecular weight.

"Film" means a microscopic gelled solid object of slab geometry.

"Microcapsule" means a microscopic (few micrometers in size to few millimeters) solid object of from a few micrometers to a few millimeters in size that is of essentially regular cylindrical shape and exhibits a liquid core and a semipermeable shell.

"Nanoparticle" means a submicroscopic solid object, essentially of regular or semi-regular shape, that is less than one micrometer in its largest dimension and exhibits a liquid core and a semipermeable shell.

"Shell" means an insoluble polymeric electrostatic complex composed of internal core polymer(s) and external bath polymer(s) molecularly bonded, or gelled, in close proximity.

"Core polymer" means an internal part of the microcapsule, nanoparticle, or polymeric film.

"Hydrogel" means a solution of polymers, sometimes referred to as a sol, converted into gel state by small ions or polymers of the opposite charge or by chemical crosslinking.

"Macrodevice" means delivery devices exhibiting relatively large size and macroscopically visible geometrical shapes, including microparticles, microcapsules, gel slabs, and polymeric coatings.

"Schiff-base" refers to a reaction between an aldehyde and carboxylic groups of two chemical species resulting in a covalent link that can undergo further modification, including reactions. For example, the link is subject to rearrangement in highly protonic or acidic, low pH environments unless a reductive reaction is performed, as with cyanoborohydrate. The Schiff-base bond is susceptible to dissociation, which forms the basis for the drug release characteristics described herein.

The following abbreviations are used for convenience: SA-HV, high viscosity sodium alginate; CS, cellulose sulfate; k-carr, kappa carrageenan; PGA, polyglutamic acid; ChS-6, chondroitin sulfate-6; F-68, Pluronic copolymer; 3PP, pantasodium tripolyphosphate; PMCG, poly (methylene-co-guanidine) hydrochloride; SH, spermine hydrochloride; PS, protamine sulfate; PDA, dextran polyaldehyde; OVA, ovalbumin (egg albumin); GMS, gentamycin sulfate; PEG, polyethylene glycol; Chit, chitosan glutamate; PBS, phosphate-buffered saline.

The invention is directed to a composition of matter comprising various polyanion and polycation mixtures. One useful combination is anionically charged alginate/CS and a polymer-bound drug and cationically charged PMCG, calcium chloride (and nonionic F-68 Pluronic). Other useful polyanions for making polymeric films, capsules, and nanoparticles are listed in copending U.S. patent application Ser. No. 09/169,459 filed Oct. 9, 1998 and entitled Micro-Particulate and Nano-Particulate Polymeric Delivery System, the contents of which are incorporated herein by reference.

A pharmaceutical composition can be prepared using a drug encapsulated in the drug delivery vehicle of the invention. The pharmaceutical composition can comprise a drug in a suitable polymeric form and a biologically acceptable matrix. Suitable polymeric forms include microcapsules, microparticles, films, polymeric coatings, and nanoparticles. Nanoparticles are particularly useful in the practice of the invention because of their small size and suitability for use in injectables formulations.

Polymers and polyelectrolytes contemplated in the practice of this invention in nanoparticulate form include copolymers of water soluble polymers, including, but not limited to, dextran, derivatives of poly-methacrylamide, PEG, maleic acid, malic acid, and maleic acid anhydride and may include these polymers and a suitable coupling agent, including 1-ethyl-3(3-dimethylaminopropyl)-carbodiimide, also referred to as carbodiimide.

The drug delivery vehicles of the invention comprise a core polymeric matrix in which a drug can be dispersed or dissolved and in which the core is surrounded by a polymeric shell. A multicomponent vehicle is formed by polyelectrolyte complexation. Drugs exhibiting charged character become an integral part of the particle. For example, an anionic antigen and multicomponent core anionic polymers become an integral part of the complex formed with receiving bath polycations. Non-charged small drugs are conveniently attached to larger molecules, preferably charged polymers.

The micro- and nanoparticles can be prepared by contacting solutions of charged droplet-forming polymers with polymers of opposite charge, wherein the contacting is by simple stirring or by capturing a mist of the droplet forming polymer in a liquid of the opposite charged polymer. The mist can be created by atomizing the charged polymer or polymer/drug conjugate with a hollow ultrasonic device to form a cloud of submicroscopic droplets ranging in size from about 0.01 to 3 nanometers. Particles prepared with a polyanionic core will have a polyanionic/polycationic complex shell and an excess positive charge on the periphery of the particle. Particles prepared with a polycationic core will have a polycationic/polyanionic complex shell and an excess negative charge on the periphery of the particle. The polymeric solutions typically are provided at a concentration of from 0.01 to 0.2 weight percent and in a ratio of from about 1:1 to 1:4.

EXAMPLE 1

Protein-Loaded Nanoparticle 1

Figure 1:
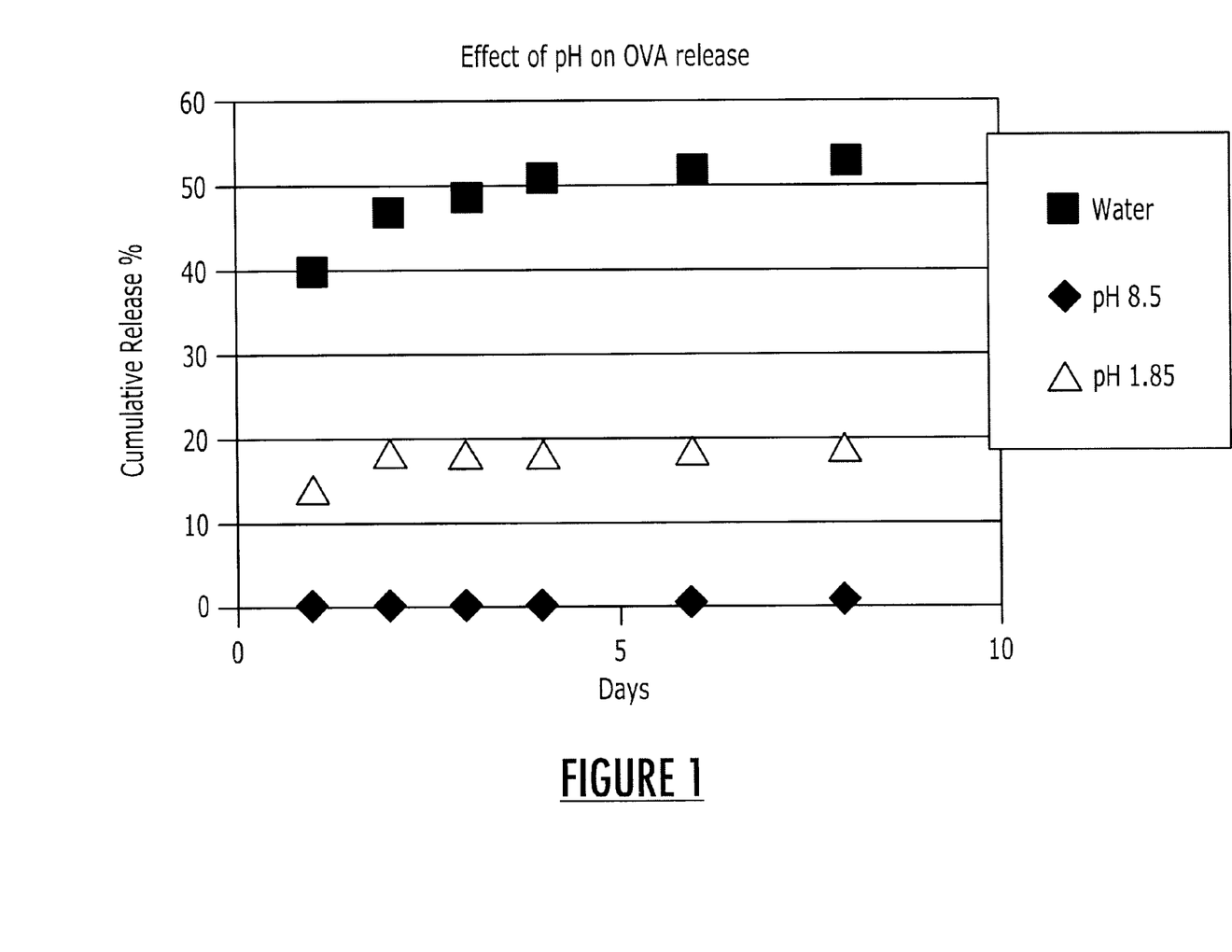
FIG. 1 is a graph showing the impact of pH on the percentage of release of egg albumin over a period of 10 days.

Particles were generated using a droplet-forming polyanionic solution composed of 0.05 wt-% HV sodium alginate (SA-HV), 0.05 wt-% CS in water, 0.4 wt-% OVA in water, and a corona-forming polycationic solution composed of 0.05 wt-% SH, 0.05 wt-% PMCG hydrochloride, 0.05 wt-% calcium chloride, and 1 wt-% F-68 in water. The polymers were high viscosity sodium alginate (SA-HV) from Kelco/Merck (San Diego, Calif.) of average molecular weight $4.6 \times 10^5$, cellulose sulfate, sodium salt (CS) from Janssen Chimica (Geel, Belgium), average molecular weight $1.2 \times 10^6$; poly(methylene-co-guanidine) hydrochloride (PMCG) from Scientific Polymer Products, Inc. (Ontario, N.Y.), with average molecular weight $5 \times 10^3$, spermine hydrochloride (SH) from Sigma, molecular weight 348.2, OVA is ovalbumin from Sigma and Pluronic P-68 from Sigma, average molecular weight 5,400. Pluronic F-68 is a water soluble nonionic block polymer composed of polyoxyethylene and polyoxypropylene segments. The particles were instantaneously formed, allowed to react for 1 hour and their size and charge evaluated in the reaction mixture. The average size was 430 nm and the average charge 15.2 mV. The particles were resuspended with different buffers (neutral pH 7, pH 1.85 and pH 8) and OVA release was measured by a colorimetric method (Bradford). FIG. 1 shows that OVA is retained at pH 7, but rapidly released at other pH's.

EXAMPLE 2

Protein-Loaded Nanoparticle 2 (Crosslinked)

Figure 2:
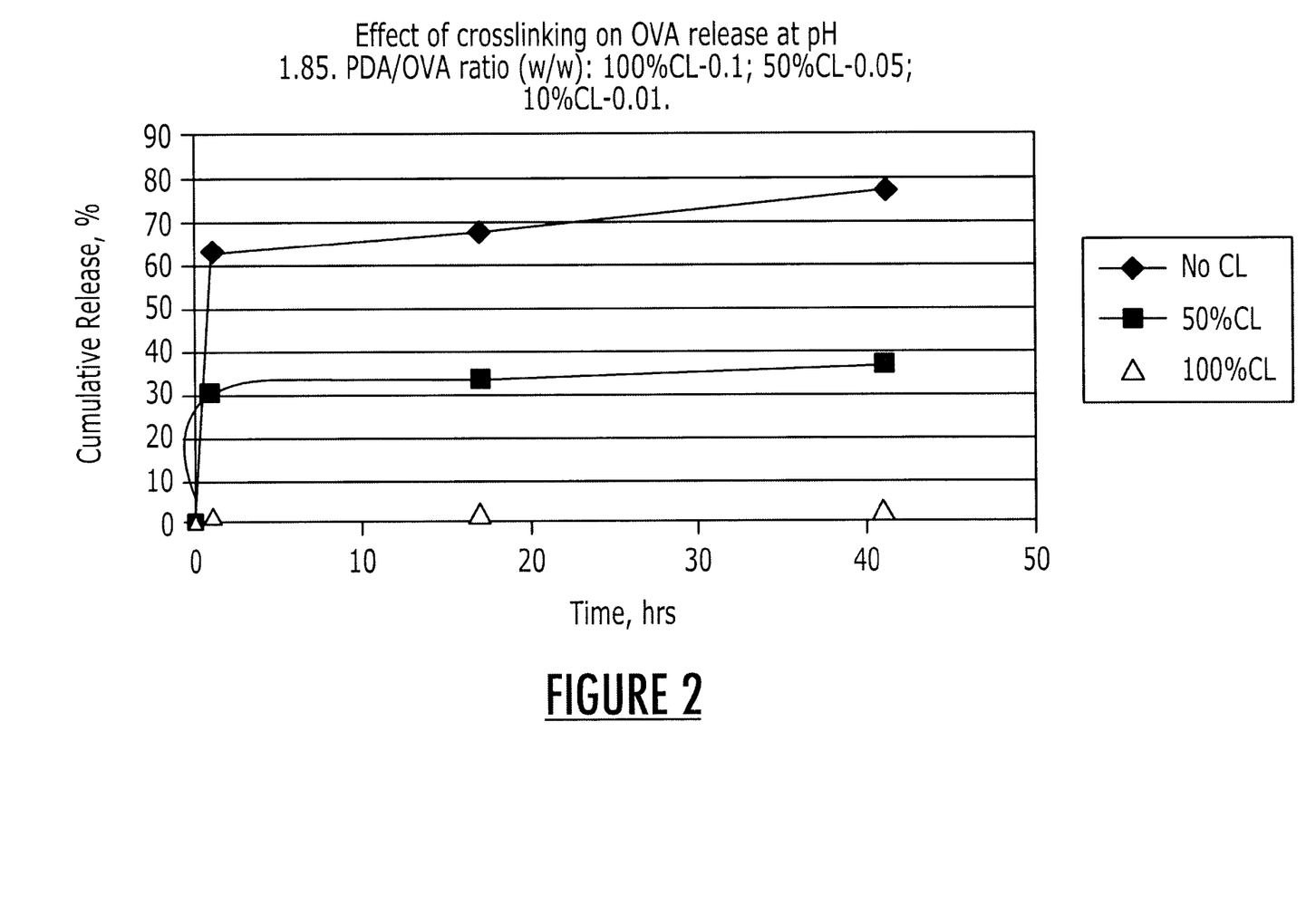
FIG. 2 shows the impact on the release rate of egg albumin at an acidic pH of the degree of crosslinking of the egg albumin with dextran polyaldheyde.

These particles were generated using same solutions as in Example 1, except the droplet forming solution contained additional polymer, DPA. DPA is dextran polyaldehyde from CarboMer (Westborough, Mass.), with an average molecular weight of 40,000. The particles were instantaneously formed, allowed to react for 1 hour and their size and charge evaluated in the reaction mixture. The average size was 330 nm and the average charge 15.5 mV. The particles were separated at 15,000 g and incubated for 30 min. in a HEPES buffer (pH 8.0) to perform the crosslinking reaction between the polymer constituents and OVA. FIG. 2 shows the effect of crosslinking on OVA release at pH 1.85. The PDA/OVA mass ratio was (from the top of figure): 0 (no crosslinking), 0.01, 0.05 and 0.1. The Schiff-base product between the anionic groups of OVA and aldehyde group of PDA allowed an adjustment of release via ion exchange as opposed to no release for permanently bound OVA (under reduction conditions with cyanoborohydrate incubation) (not shown). When the reduction step was performed no release was noted under any condition. Similar results (as shown in FIG. 2) were obtained when the anionic solution was first pre-incubated at pH 8.0 for 30 minutes and the particles formed after incubation of the solution.

EXAMPLE 3

Use of Protein-Loaded (and PDA-Crosslinked) Nanoparticles for Oral Antigen Delivery These particles were generated using same solutions as in Examples 1 and 2. Eight different batches were prepared:

(1) PDA/OVA mass ratio=0 (no crosslinking)
(2) PDA/OVA mass ratio=0.01
(3) PDA/OVA mass ratio=0.05
(4) PDA/OVA mass ratio=0.1
(5) PDA/OVA mass ratio=0.01 (plus reduction with cyanoborohydrate)
(6) PDA/OVA mass ratio=0.05 (plus cyanoborohydrate)
(7) PDA/OVA mass ratio=0.1 (plus cyanoborohydrate)
(8) PDA/OVA mass ratio=0 (no OVA, no crosslinking)
(9) Soluble OVA Once the particles were generated and washed they were introduced orally into experimental animals (male Sprague-Dawley adult rats (200–250 g wt., 12–15 weeks old, Harlow). Ten animals were used for each group. About 1 mg of dry weight of nanoparticles in the reaction mixture has been administered orally into the stomach of each animal. The nonloaded (#8) nanoparticles were also administered to control animals, in addition to a soluble antigen (OVA)(#9). ELISA assay of secretory IgA and serum IgG antibodies was carried out as described [Challacombe, et al., Enhanced secretory IgA and systemic IgG antibody response after oral immunization with biodegradable microcapsules containing antigen. *Immunology* 76: 164–168 (1992)]. Primary and secondary immunization protocol was used, consisting of two immunizations at week 0 and at week 4. Immunizations with OVA-nanoparticles (and PDA Schiff-base crosslinked, batch nos. 2 through 4) resulted in dramatically greater levels of both secretory and serum antibodies (about 30–50 times) than those found with the soluble antigen (Table 1). In another set of experiments nonloaded nanoparticles (no OVA) were separately tested in simulated gastric (pH 2) and intestinal (pH 8.3) solutions for their stability. The nanoparticles remained stable during the observation period of one week. However, a separate experiment revealed that OVA-loaded nanoparticles, but not crosslinked (#1) released about 40% OVA in 2 hours at pH 2 (20% at pH 8.3) and continued to release thereafter. #5–7 batches did not release any OVA during that time. Similar results in terms of antibodies and release characteristics were obtained for tetanus toxoid antigen.

TABLE I

Response to oral delivery of nanoparticulate OVA antigen (R = Reduced; sol = soluble)

| PDA/OVA | | 0 | 0.01 | 0.05 | 0.1 | 0.01(R) | 0.05(R) | 0.1(R) | 0 (no OVA) | Sol OVA |
|---|---|---|---|---|---|---|---|---|---|---|
| Day 28 | Mean | 88.0 | 146.0 | 230.0 | 450.0 | 96.0 | 180.0 | 356.0 | 66.0 | 75.0 |
|  | SD | 23.0 | 53.0 | 22.0 | 24.0 | 43.0 | 26.0 | 33.0 | 22.0 | 26.0 |
| Day 56 | Mean | 812.0 | 1,243.0 | 8,467.0 | 10,235.0 | 856.0 | 6,556.0 | 8,561.0 | 615 | 550.0 |
|  | SD | 36.0 | 487.0 | 614.0 | 815.0 | 24.0 | 450.0 | 651.0 | 21.0 | 38.0 |

EXAMPLE 4

Covalent Conjugate of Small Drug Molecule with Polymer

Gentamycin sulfate, GMS (Sigma), is a small molecular weight drug with molecular weight 710. If incorporated into nanoparticles formed in a reverse system (core polymer cationic, corona polymer anionic) GMS will be quickly released. If a conjugate to a noncharged polymer is then made a slow-down of release is observed following its nanoparticulate formulation. 50 mg of gentamycin sulfate is dissolved in 2.5 ml water and pH adjusted to alkalic by means of 0.53 M $NaHCO_3$. The final volume was 3.5 ml and bicarbonate concentration 0.1 M. 100 mg AKM-1510 maleic anhydride-PEG polymer (Shearwater Polymers, Huntsville, Ala.; average molecular weight 14,000) is added to GMS solution and kept at 4° C. under stirring. The product was dialyzed against water (800 ml, twice) at 4° C. This product exhibits an antimicrobial activity similar to that of free GMS as assayed by in vitro disc diffusion assay using a test organism on agar plates (*Bacillus subtilis*) [Deacon, S. Assay of gentamicin in cerebrospinal fluid, Journal of Clinical Pathology 29: 749–751 (1976)].

EXAMPLE 5

Nanoparticles Loaded with GMS-Polymer Conjugate

Figure 3:
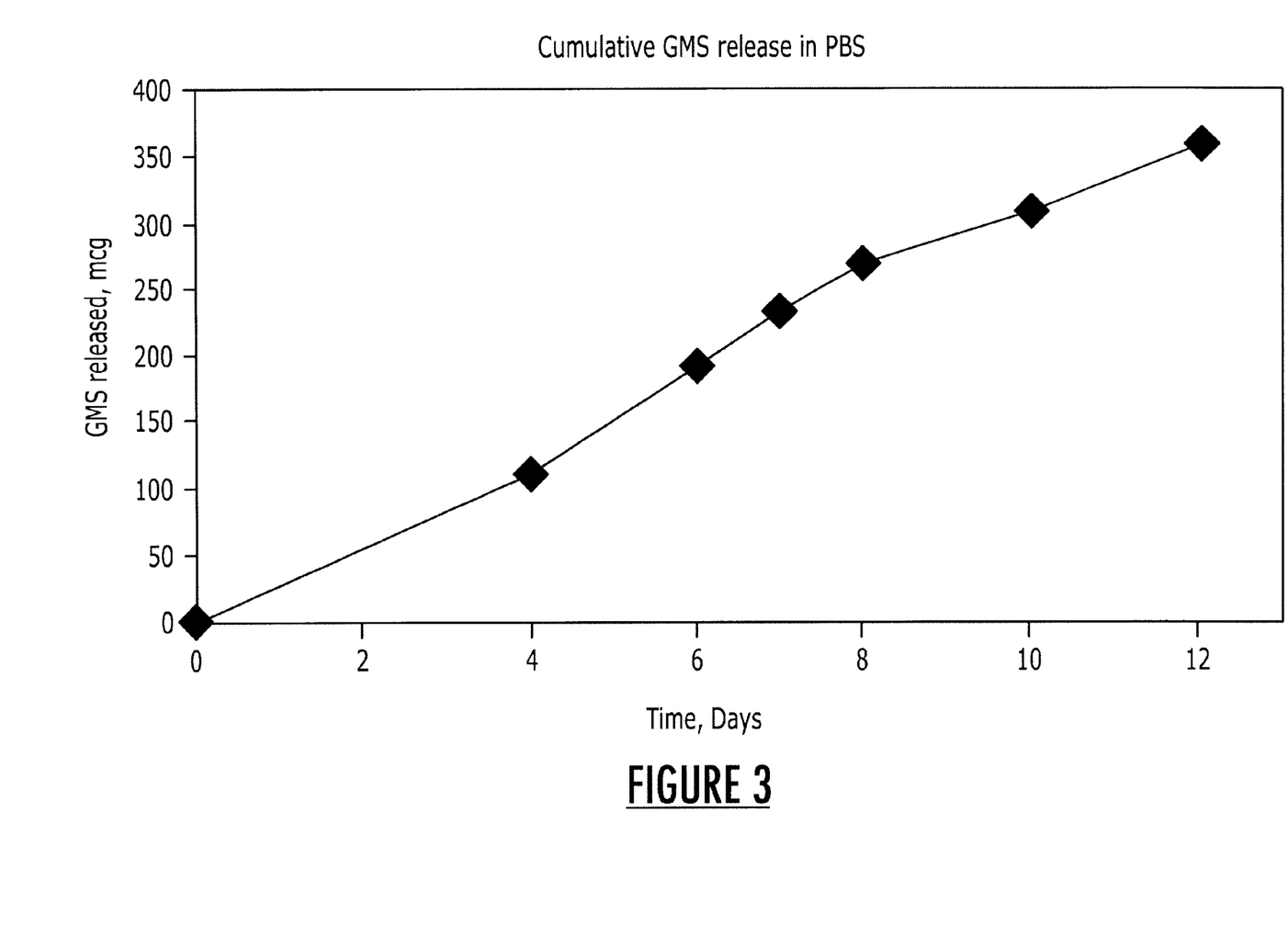
FIG. 3 shows the release rate of gentamycin sulfate from nanoparticles of the invention in a phosphate buffered saline solution.

Such particles were generated using a droplet-forming polyanionic solution composed of 0.025 wt-% SA-HV and 0.025 wt-% CS in water (and GMS, see below) and corona-forming polycationic solution composed of 0.05 wt-% SH, 0.065 wt-% PMCG, 0.05 wt-% calcium chloride and 1 wt-% F-68 Pluronic in water. The working anionic solution contained 5.4 ml of the above anionic solution and 0.6 ml of dialyzed conjugate (prepared in Example 3). The particles were instantaneously formed, allowed to react for 1 hour and their size and charge evaluated in the reaction mixture. The average size was 420 nm and the average charge 15.4 mV. The particles were collected by centrifugation at 15,000 g for 20 min. The resulting 1-ml suspension contained about 5.7 mg GMS incorporated into nanoparticles. The GMS release in buffer of pH 6.8 (PBS) was assessed via an efflux method in vitro using 5-ml test buffer (PBS) on a shaker. Samples were withdrawn at different time intervals and the amount withdrawn replaced by a fresh buffer. FIG. 3 shows that GMS is released at about 50 µg/day, representing about 5%/day of the total entrapped amount. The amount of released GMS is based on the disc diffusion assay as in Example 3. Similar data were collected on the basis of antibody assay of GMS (Syva-Behring, San Jose, Calif.).

EXAMPLE 6

Drug Release upon an Enzyme Action

The nanoparticles were prepared using a droplet-forming polyanionic solution composed of 0.125 wt-% 3PP and 0.125 wt-% k-carr (and GMS, see below) and corona-forming polycationic solution composed of 0.05 wt-% Chit, 0.1 wt-% calcium chloride and 1 wt-% Pluronic F-68 in water. Chitosan glutamate (Protasan HV) is from Pronova Biopolymers/FMC Corp., Drammen, Norway and k-carrageenan X52 from Sanofi Bio-Industries, Paris, France. The working anionic solution contained 19.2 ml of the above anionic solution and 4.8 ml of dialyzed conjugate (prepared in Example 3). The particles were instantaneously formed, allowed to react for one hour and their size and charge evaluated in the reaction mixture. The average size was 245 nm and the average charge was 13.4 mV. The particles were collected by centrifugation at 15,000 g for 20 min. The resulting 1-ml suspension contained about 4.9 mg GMS. The GMS release was assessed as in Example 5. There was essentially no release of GMS in PBS buffer because of the particles are very compact and impermeable. In order to allow for GMS release, particles were digested by an enzyme attacking chitosan, lysozyme. A stock solution of lysozyme contained 1 mg/ml of lysozyme (Sigma, 47.103 units/mg) in 1 ml PBS buffer. 50 µl of nanoparticulate suspension was mixed with 450 µL of diluted stock solution to give final 0.1 µg/µL, 1 µg/µL and 10 µg/µL of lysozyme. Solutions were incubated 3 hours at 37° C., separated by centrifugation and their GMS release assessed. GMS release was estimated to be 25 µg/day.

Similar results were obtained for nanoparticles incorporating GMS conjugate but containing chondroitin sulfate (Sigma) as a component which is degradable by the action of hyaluronidase (Sigma) enzyme. Again, no GMS release was noted for nanoparticles in PBS buffer, but some release was observed for enzyme-treated vehicle.

When similar preparation was formulated, this time containing OVA protein, an increased release of GMS was observed for protease-treated nanoparticles as compared to smaller release for protein-free nanoparticles.

The above enzyme-released drug can be affected by certain bodily sites where such enzymatic activity is often displayed. Ocular-site or serum (intravenous application, [Varum, K. M., Myhr, M. M., Hjerde, R.-J., Smidsrod, S. In vitro degradation rates of partially N-acetylated chitosans in human serum, Carbohydrate Research 299: 99–101 (1997)] is likely candidate site for lysozyme-triggered nanoparticulate digestion and wound- (tumor-) site for protease-facilitated action.

EXAMPLE 7

Taxol Formulation and Release

Taxol (Paclitaxel, Sigma) is water-insoluble substance used for cancer treatment. A water-soluble derivative was synthesized (by an in-house technology) and covalently linked to a biodegradable polymer (PGA, Sigma, molecular weight 30,000). When bound to this polymer, Taxol-conjugate is inactive, rendering it less toxic to animals than Taxol, even when delivered at doses much higher than the maximally tolerated doses of Taxol. Water-soluble Taxol-polymer conjugate is then formulated into nanoparticles. The nanoparticles were generated using similar formula as mentioned in Example 3, except an additional polymer has been added to the core-forming polymeric mixture, 0.1 wt-% Taxol-PGA conjugate. Isolated nanoparticles were tested in vitro and shown to inhibit growth of a cancer-derived Meth-A fibroblastoma cell line.

EXAMPLE 8

Gel Film Loaded with Plasmid DNA for Gene Transfer

A mold method, using the 1.5 ml Pierce (Rockford, Ill.) dialysis cassettes (with 10 k molecular weight cut-off) was been developed. A water solution of core polymers was prepared by weighing 0.6 g of CS, 0.6 g of high viscosity sodium alginate (Algin), 100 $\mu$g pCEPluc plasmid (modified commercial plasmid, containing CMV promotor in which luciferase enzyme was cloned in as a reporter gene), and dissolving them for one hour in 100 cc of PBS by means of a magnetic bar and stirrer plate. This solution also contained different amounts of PDA. A cationic shell solution consisting of 1 g of calcium chloride and 1 g of poly(methylene-co-guanidine) hydrochloride in 100 cc of water was also prepared. The polymers used were: high viscosity sodium alginate (SA-HV) from Kelco/Merck (San Diego, Calif.) of molecular weight $4.6 \times 10^5$; cellulose sulfate, sodium salt (CS) from Janssen Chimica (Geel, Belgium) having an average molecular weight $1.2 \times 10^6$; and poly(methylene-co-guanidine) hydrochloride from Scientific Polymer Products, Inc. (Ontario, N.Y.), with average molecular weight $5 \times 10^3$. 1.5 ml of the core solution was incorporated via an injection port on the cassette. The cassette was then dipped in 150 ml of cationic solution and allowed to react for three hours.

Oligomers of cation and small inorganic cations penetrated through the dialysis membrane of the cassette and reacted with the internal core solution. The membrane was formed under aseptic conditions using sterile cassettes. The core solution is filter-sterilized (0.2 $\mu$m) prior to the application. After processing, the gelled film was aseptically cut off the cassette. The resulting semitransparent film was stable for many weeks in PBS solution. Since such films possess a positive charge, they were coated with diluted anionic polymers to introduce a negative charge. Two suitable anionic polymers are alginate (0.1% w/w) or carboxymethylcellulose (0.1% w/w), both exhibiting nonadhesive (tissue) properties. The coating was carried out by means of dipping the polymeric film into the above solution for 5 minutes, followed by a quick wash in PBS solution. Alternatively, polymeric films were coated with 1/6 concentration of the anionic Algin/CS solution as mentioned above. The films were stored in a moist state in a covered sterile Petri dish. In a separate experiment, polymeric films of a similar composition were prepared using 5 and 15 ml (maximum capacity) cassettes.

Animals, Implantation and Luciferase Assay. Formulated plasmid was delivered subcutaneously (sq), via a surgery, into a rat model (Sprague-Dawley, 200–300 g, male). Each animal had two implants (one implant on each side). The animals were housed in the MCN Animal Care Facility (Vanderbilt University) and maintained according to the American Association for Accreditation of Laboratory Animal Care standards. All procedures were carried out aseptically and were approved under the guidelines of the local Animal Care and Use Committee. Following the application, animals were harvested at 24, 48, 72, 120 and 168 hr and tissue below the implant harvested by means of a biopsy punch. The harvested material was exposed to a lysis buffer, homogenized mechanically and extracted. The luciferase assay was carried out with help of Sigma assay kit and a luminometer (Monolight 2010 Luminometer, Analytical Luminescence Lab., San Diego, Calif.). Data were normalized by protein (bicinchoninic acid, Pierce). Results are presented in Table II.

TABLE II

| Gene Transfer from plasmid encapsulated into polymeric films | | | | | |
|---|---|---|---|---|---|
| Hr | 24 | 48 | 72 | 120 | 168 |
| Soluble plasmid (no film) | 1,200 | 4,325 | 1,926 | 555 | — |
| PDA/plasmid 0 (w/w) | 2,250 | 93,584 | 125,455 | 52,356 | 1,535 |
| PDA/plasmid 0.05 (w/w) | 3,355 | 109,265 | 142,864 | 87,523 | 15,256 |
| PDA/plasmid 0.1 (w/w) | 4,686 | 155,111 | 115,723 | 96,325 | 25,864 |

Added PDA allowed for a sustained release of plasmid and extension of expression beyond the period of two days, typically exhibiting a maximum for soluble plasmid. Similar results were obtained when nanoparticles were used as a gene delivery vehicle. Thus, animals, including humans, can be immunized by orally delivering an encapsulated antigen in the particles as described in which the particles, which include a Schiff base PDA-crosslinked antigen, are taken up in the intenstinal tract and result in an increase in secretory and systemic antibodies in the blood.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for preparing microparticles and nanoparticles comprising the steps of
   (a) forming a covalent conjugate of a drug and a droplet-forming polymer; and
   (b) forming microparticles or nanoparticles having a shell and a core of opposite charge, each having at least two charged polymers and in which the conjugate is contained within the core, said microparticles or nanoparticles formed by
      (i) providing a stream of uniformly-sized drops of the charged droplet forming polymer;
      (ii) collecting those droplets in a stirred reactor provided with a polymeric solution of opposite charge, and
      (iii) reacting the droplets and the solution to form the particles.

2. The method of claim 1 wherein the conjugate comprises one of the charged polymers of the core.

3. The method of claim 1 wherein the polymers of the shell and core are crosslinked by a Schiff-base reaction.

4. The method of claim 3 wherein the crosslinking step is accomplished by incubating the particles at a pH of about 8 for a period of time sufficient to cause said crosslinking.

5. The method of claim 4 wherein the time period is about 30 minutes.

6. The method of claim 3 wherein the crosslinking step is accomplished by reacting at least one charged polymer with a crosslinking polymer prior to formation of the particles.

7. The method of claim 1 wherein the particle size of the drops is from about 5 to 15 microns.

8. The method of claim 1 in which the droplet forming polymer is a cationically charged polymer.

9. A pharmaceutical composition for drug release comprising a multipolymeric drug delivery vehicle selected from the group consisting of microparticles, microcapsules, nanoparticles and film vehicles, said vehicle comprising a core having at least two charged polyelectrolytes and a shell surrounding the core, said shell having at least two polyelectrolytes of opposite charge to the charge of the core polyelectrolytes, the vehicle exhibiting a charged surface and said core further comprises covalently crosslinked conjugates of a drug and of one or more polymers, wherein anionic polyelectrolyte components suitable for use in said vehicle include components selected from the group consisting of sodium alginate, cellulose sulfate, pantasodium tripolyphosphate, kappa carrageenan and mixtures thereof and cationic polyelectrolyte components suitable for use in said vehicle include components selected from the group consisting of poly(methylene-co-guanidine) hydrochloride, spermine hydrochloride, calcium chloride and mixtures thereof.

10. The pharmaceutical composition of claim 9, wherein said cationic polyelectrolyte components further comprise a water soluble non-ionic polymer derived from polyoxyethylene and polyoxypropylene units.

11. The pharmaceutical composition of claim 9, wherein said anionic polyelectrolyte composition comprises a mixture of sodium alginate and cellulose sulfate and said cationic polyelectrolyte component comprises a mixture of poly(methylene-co-guanidine) hydrochloride and calcium chloride.

* * * * *

UNITED STATES PATENT AND TRADEMARK OFFICE
CERTIFICATE OF CORRECTION

PATENT NO. : 6,589,563 B2
DATED : July 8, 2003
INVENTOR(S) : Prokop

It is certified that error appears in the above-identified patent and that said Letters Patent is hereby corrected as shown below:

Column 10,
Line 56, "those" should read -- these --.

Column 11,
Line 8, "claim 1" should read -- claim 7 --.

Signed and Sealed this

Twenty-fifth Day of November, 2003

JAMES E. ROGAN
*Director of the United States Patent and Trademark Office*